United States Patent
Hahn et al.

(10) Patent No.: US 6,787,047 B1
(45) Date of Patent: Sep. 7, 2004

(54) METHODS FOR MANUFACTURING A MICROSTRUCTURED SENSOR

(75) Inventors: Dietmar Hahn, Gerlingen (DE); Gottfried Flik, Leonberg (DE); Alexandra Jauernig, Yokohama (JP)

(73) Assignee: Robert Bosch GmbH, Stuttgart (DE)

( * ) Notice: Subject to any disclaimer, the term of this patent is extended or adjusted under 35 U.S.C. 154(b) by 215 days.

(21) Appl. No.: 09/707,332

(22) Filed: Nov. 7, 2000

Related U.S. Application Data (62) Division of application No. 09/036,733, filed on Mar. 9, 1998, now abandoned.

(30) Foreign Application Priority Data

Mar. 13, 1997 (DE) .......................................... 197 10 358

(51) Int. Cl.$^7$ .............................................. G01N 27/00
(52) U.S. Cl. ....................... 216/2; 204/192.21; 205/122; 205/157; 205/162; 205/164
(58) Field of Search ................................. 338/22 R, 34; 216/2; 204/192.21; 205/122, 157, 162, 164

(56) References Cited

U.S. PATENT DOCUMENTS

| | | | | |
|---|---|---|---|---|
| 4,510,036 A | | 4/1985 | Takeuchi et al. ............. 204/425 |
| 4,732,738 A | * | 3/1988 | Nakatani et al. ............... 422/94 |
| 4,900,405 A | | 2/1990 | Otagana et al. ................ 204/17 |
| 5,140,393 A | | 8/1992 | Hijihigana et al. ............ 357/25 |
| 5,227,012 A | * | 7/1993 | Brandli et al. ................. 216/16 |
| 5,481,636 A | * | 1/1996 | Fukuda et al. ............... 385/122 |
| 5,547,556 A | | 8/1996 | Kobayashi et al. ......... 204/426 |

FOREIGN PATENT DOCUMENTS

| | | | | |
|---|---|---|---|---|
| GB | 2 220 074 | | 12/1989 | |
| GB | 2220074 A | * | 12/1989 | .......... G01N/27/12 |
| JP | 05090646 A | * | 4/1993 | ........... H01L/35/00 |

OTHER PUBLICATIONS

Hofmann, T. et al. "Fluid characterization using sensor elements based on interdigitated electrodes" Sensors and Actuators B 37, No. 1–2, 1996 pp 37–42.*

Schutze, A. et al "A new microstructured silicon substrate for ultrathin gas–sensitive films" Sensors and Actuators A 37–38, 1993, pp 751–755.*

(List continued on next page.)

Primary Examiner—Anita Alanko
(74) Attorney, Agent, or Firm—Kenyon & Kenyon (57) ABSTRACT

A method for manufacturing a sensor, the sensor including a three-dimensional interdigital electrode arrangement positioned on a substrate, comprising applying a temperature sensing resistor onto the substrate by sputtering a first adhesion layer and a first metallic layer onto the substrate, applying a first resist layer to the first metallic layer, applying and structuring a first resist material on the first metallic layer, and after structuring, etching the first metallic layer in resist free areas; and applying a three-dimensional interdigital electrode arrangement onto the substrate by sputtering a second adhesion layer and a second metallic layer onto the substrate, applying and structuring a second resist material only to second metal layer, after the structuring, etching the second metallic layer in resist free areas to form valleys, and after etching the second metallic layer, applying an electroplating layer.

25 Claims, 7 Drawing Sheets

OTHER PUBLICATIONS

Howe, R.T., Wescon/89; Silicon microdynamic systems–recent development in microactuators and micromachinery, pp 202–205, Nov. 14–15, 1989.*

Sheppard, N. F., Jr. et al "Electrical Conductivity Measurements Using Microfabricated Interdigitated Electrodes" Anal. Chem., May 1993, 65 (9) 1199–1202.*

Binder, J. "New generation of automotive sensors to fulfil the requirements of fuel economy and emission control" Sensors and Actuators A, 1992, vol. A31, pp. 60–67.*

Kolesar, Jr. et al "Interdigitated Gate Electrode Field Effect Transistor for the Selective Detection of Nitrogen Dioxide and Diisopropyl Methylphosphonate" Anal. Chem., Nov. 1989, 61 (21) 2355–2361.*

Ralston, A.R.K. et al, "Electrical Characteristics of Plasma Deposited SiO2 Films Produced in an ECR Reactor from Silane/O2 or TEOS/O2 Gas Mixtures" IEEE Conference Record—Abstracts. 1995 IEEE Int'l Conf on Plasma Science, Jun. 1995, p. 181.*

Fouke, J.M. et al "Sensor for Measuring Surface Fluid conductivity In Vivo" IEEE Trans on Biomedical Engr., Oct. 1988, 35 (10) 877–880.*

Sheppard, Jr., N.F., et al "Method of a Conductimetric Urea Sensor" Proceedings of the 1993 IEEE Nineteenth Annual Northeast Bioengineering Conf., 1993, Mar. 18–19, 1993, pp 191–192.*

"New Generation of Automotive Sensors to Fulfil the Requirements of Fuel Economy and Emission Control", J. Binder, Sensors and Actuators, Elsevier Sequoia, Lausanne, vol. A31, 1992, pp. 60–67.

* cited by examiner

METHODS FOR MANUFACTURING A MICROSTRUCTURED SENSOR

This application is division of Ser. No. 09/036,733 filed Mar. 9, 1998 now abandoned.

FIELD OF THE INVENTION

The present invention relates to a sensor for conductivity and capacitance measurement in gases or liquids.

BACKGROUND INFORMATION

Combined conductivity and capacitance measurements in fluids are important, for example, in characterizing gasoline/methanol mixtures, ascertaining the water content in brake fluids, analyzing battery acids, and determining oil degradation using a measurement of alkaline reserve. Since conductivity, in particular, exhibits temperature dependency, analyses of this kind should advantageously be coupled with temperature measurements. A combination of conductivity, capacitance, and temperature measurements to characterize gasoline/methanol mixtures is described in the article "New Generation of Automotive Sensors to Fulfil the Requirements of Fuel Economy and Emission Control", J. Binder, Sensors and Actuators, Vol. 31, Elsevier Sequola, Lausanne, 1992, pp. 60–67, and has been carried out as a sensor. This sensor is, however, large and very complex in configuration.

SUMMARY OF THE INVENTION

The present invention relates to a sensor, in particular for conductivity and capacitance measurement in gases or liquids, having a three-dimensional interdigital electrode arrangement located on a substrate. The sensor additionally has an integrated temperature resistor and preferably also an integrated heating resistor. The temperature resistor, preferably configured in meander fashion, is used to measure temperature in liquids or gases. The heating resistor, also preferably configured in meander fashion, is used to heat the gas and the liquid between the interdigital electrodes or to heat a sensitive material which has been introduced into the electrode structure (for example by pressure technology). Depending on the intended application, for example analysis of gasoline/methanol mixtures, oil monitoring, etc., the heating resistor can be left out in order to simplify the structure.

The present invention advantageously provides for the substrate to be made of silicon, such that the latter can already contain an integrated analysis circuit. Other substrates such as ceramic, glass, or plastics can, however, also be used advantageously depending on the application.

The present invention provides for a miniaturized sensor which can be used to characterize a plurality of liquids and gases, in which the analysis is based on conductivity and capacitance measurements in fluids or gases, either directly or of a chemically sensitive substance between the electrodes. Advantageously, the three-dimensional electrode configuration makes possible a higher sensor sensitivity and lesser sensitivity to interference, as well as miniaturization. The sensor according to the present invention can be manufactured with high precision using a combination of process steps known per se; advantageously, when silicon is used as the substrate, a silicon electronic analysis circuit can also be integrated onto the chip (substrate) in the course of manufacture.

The present invention also concerns an expansion of the sensor depicted, in which a sensitive layer or a multilayer system is provided between the interdigital electrodes. One application that can be implemented, for example, in this context is a moisture sensor, which can be implemented by deposition of a polymer. The water uptake of the polymer causes a change in the dielectric constant, which can be ascertained by way of a change in capacitance. The purpose of the heating resistor located under the interdigital structure is to remove moisture that has collected in the polymer, so as to regenerate the sensitive layer. In addition to the application as a moisture sensor, chemical sensors in the area of fluid or gas analysis are also generally achievable. A series of sensitive layers, for example metal oxides, must be heated for operation thereof, which is controlled by the underlying heating resistor and monitored by the temperature resistor.

The present invention also concerns a method for direct boiling-point determination in liquids. One practical area of application here is, for example, the determination of the quality of brake fluids in motor vehicles. In the measurement method according to the present invention, a small volume of liquid is heated by a microstructured heating resistor, preferably inside a three-dimensional interdigital electrode structure, and the temperature is measured using an integrated microstructured temperature resistor. The interdigital electrode structure is used to determine the capacitance and resistance of the liquid in the presence of direct current and at different measurement frequencies. Since these variables are temperature-dependent, rising temperature results in higher capacitance and lower resistance. Opposite behavior occurs in the vicinity of the liquid's boiling point. Resistance rises with heating, and capacitance drops. In extreme cases, the liquid boils between the electrodes, which is associated with gas formation. Since the gas bubbles have very different dielectric characteristics from the liquid, unequivocal decreases in capacitance and increases in resistance occur upon boiling. From these changes in capacitance and resistance, the boiling temperature is determined by way of the integrated temperature resistor. An advantage of the sensor, because of the miniaturized structure, is that there is very little beat input into the liquid. In addition, because of the low heat capacity of the overall structure, very rapid measurement (on the order of seconds) is possible.

The present invention also concerns a method for manufacturing a sensor having a three-dimensional interdigital electrode arrangement located on the substrate, in particular an aforementioned sensor, such that a temperature resistor and optionally a heating resistor, preferably made of platinum, nickel, TaNi, or silver, is arranged on one surface of the substrate (the front or back side). A three-dimensional interdigital electrode arrangement, made for example of platinum or gold for highly corrosive media or of silver, copper, nickel, or aluminum for less corrosive media, is arranged on the same or the other side of the substrate. The method according to the present invention provides for a combination of various sputtering, etching, passivating, electroplating, and photolithography steps. The method can also be used, to the extent set forth, for the manufacture of simplified sensors without a heating resistor.

According to a preferred exemplary embodiment, the present invention provides in particular for both surfaces of the substrate to be coated with $SiO_2$ and $Si_3N_4$ before application of the temperature resistor onto one surface of the substrate, for example the back side, and of the electrode arrangement onto its other surface.

In particularly advantageous fashion, provision is made for manufacturing the temperature resistor, for example on the back side of the substrate, by sputtering an adhesion layer and a platinum layer onto the $SiO_2$ and $Si_3N_4$ layer that is preferably present. Subsequent thereto, a resist material is applied and structured. Etching of the platinum layer to structure the temperature resistor, and passivation of the temperature resistor with $SiO_2$, then take place. Following the passivation step, the present invention provides, advantageously and in a preferred exemplary embodiment, for the temperature resistor to be annealed to establish and stabilize the temperature coefficient.

In a further preferred exemplary embodiment of the present invention, an aforementioned method is provided such that the three-dimensional interdigital electrode arrangement is manufactured on, preferably, the front side of the substrate by first photolithographically defining an electrode region on the front side of the substrate. In the region defined in this fashion, the $SiO_2$ and $Si_3N_4$ layers which are preferably present there are etched. An adhesion and electroplating initiator layer is then sputtered on. Following sputtering, a (preferably thick) resist layer for configuration of the electrode arrangement is structured in such a way as to form resist valleys. The resist valleys manufactured in this fashion are plated out with electrode material. The resist mask is then removed and the electroplating initiator layer is etched. After subsequent anisotropic etching of the silicon substrate in the region of the electrode arrangement, preferably the contact connections are exposed and the sensors are isolated.

DETAILED DESCRIPTION OF THE INVENTION

Figure 1:
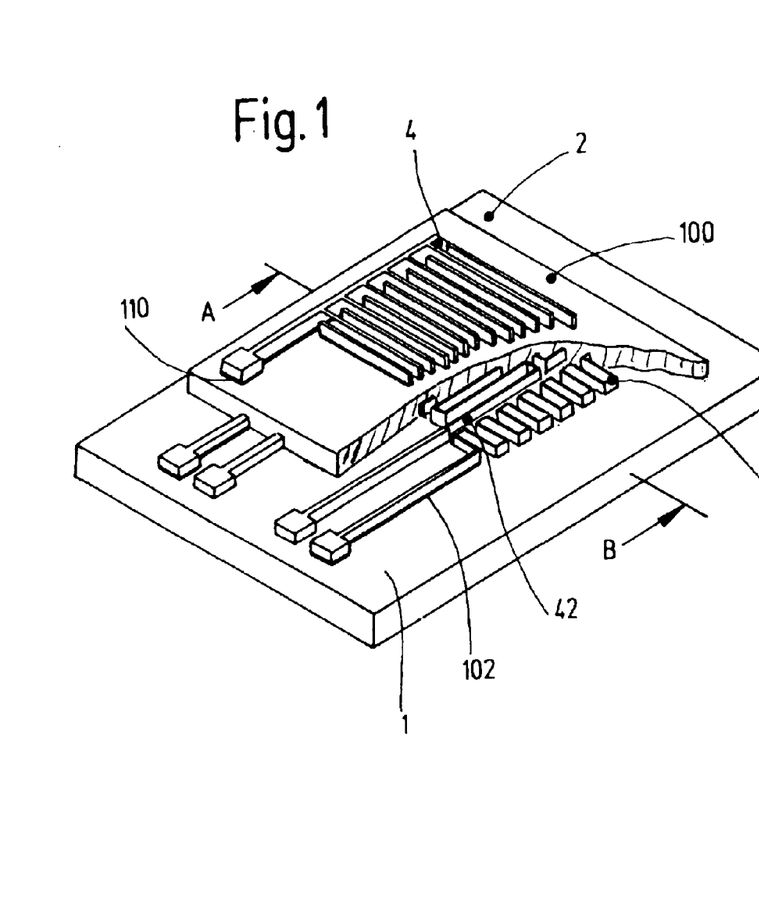
FIG. 1 shows a sensor according to the present invention.

FIG. 1 shows a substrate 2, for example made of silicon, glass, ceramic, or plastic. Structured on substrate 2, optionally using further insulation and adhesion layers 102 (when silicon is used as the substrate) is a meander-shaped heating resistor 42 around which a temperature resistor 24, also meander-shaped and preferably made of platinum, nickel, TaNi, or silver, is arranged. For insulation, a passivation layer 100 is provided on heating resistor 42 and on temperature resistor 24. For better heat transfer, the material used here is one which has not only good insulation properties but also good thermal conductivity properties. A three-dimensional interdigital electrode arrangement 4 is provided on passivation layer 100 above heating resistor 42. An adhesion and electroplating initiator layer 110 is also depicted.

Figure 2:
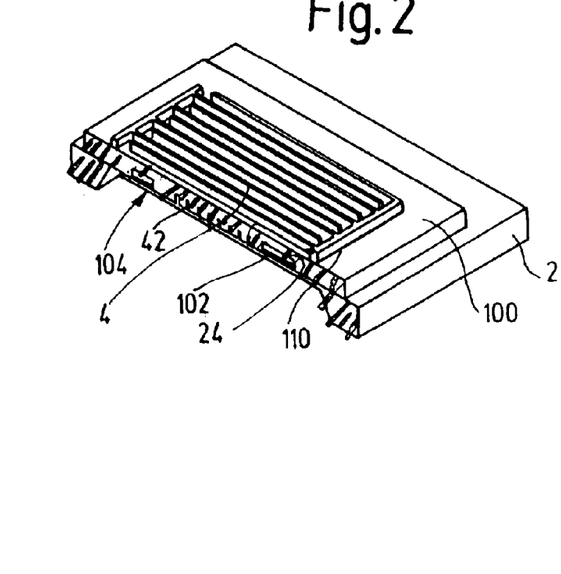
FIG. 2 shows a side view of a sensor according to the present invention based on a silicon substrate.

FIG. 2 shows a sensor according to the present invention in a side view, silicon being used here as substrate 2. The sensor comprises interdigital electrode structure 4, heating resistor 42, and temperature resistor 24, as well as additional insulation, adhesion, and contact layers. To achieve the least possible heating of the fluid, and thus also low power loss in the sensor, heating resistor 42, temperature resistor 24, and interdigital three-dimensional electrode structure 4 are arranged on a membrane 104 made of $SiO_2$ and $Si_3N_4$. Membrane 104 is implemented by anisotropic etching of silicon substrate 2.

Figure 3:
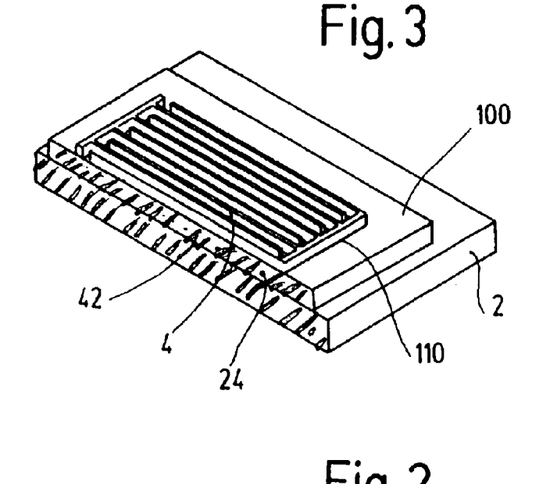
FIG. 3 shows a side view of a sensor according to the present invention based on glass, ceramic, or plastic substrates.

FIG. 3 shows a sensor according to the present invention in a side view, glass or plastic being used here as the substrate materials. The sensor comprises interdigital electrode structure 4, heating resistor 42 and temperature resistor 24, as well as additional insulation, adhesion, and contact layers. Because of the low thermal conductivity of substrate 2 ("thermal insulators"), heating of the fluid occurs essentially directly via heating resistor 42 within interdigital structure 4. It is not necessary to arrange heating resistor 42, temperature resistor 24, and interdigital electrodes 4 on a membrane.

FIGS. 1, 2 and 3 show example embodiments of the present invention, in which the surface area of the vertical surfaces of the three dimensional interdigital electrode is greater than the surface area of the top, horizontal surface. Also the height of each respective one of the electrodes of the interdigital electrodes is greater than the width of the respective electrode.

Figures 4, 5:
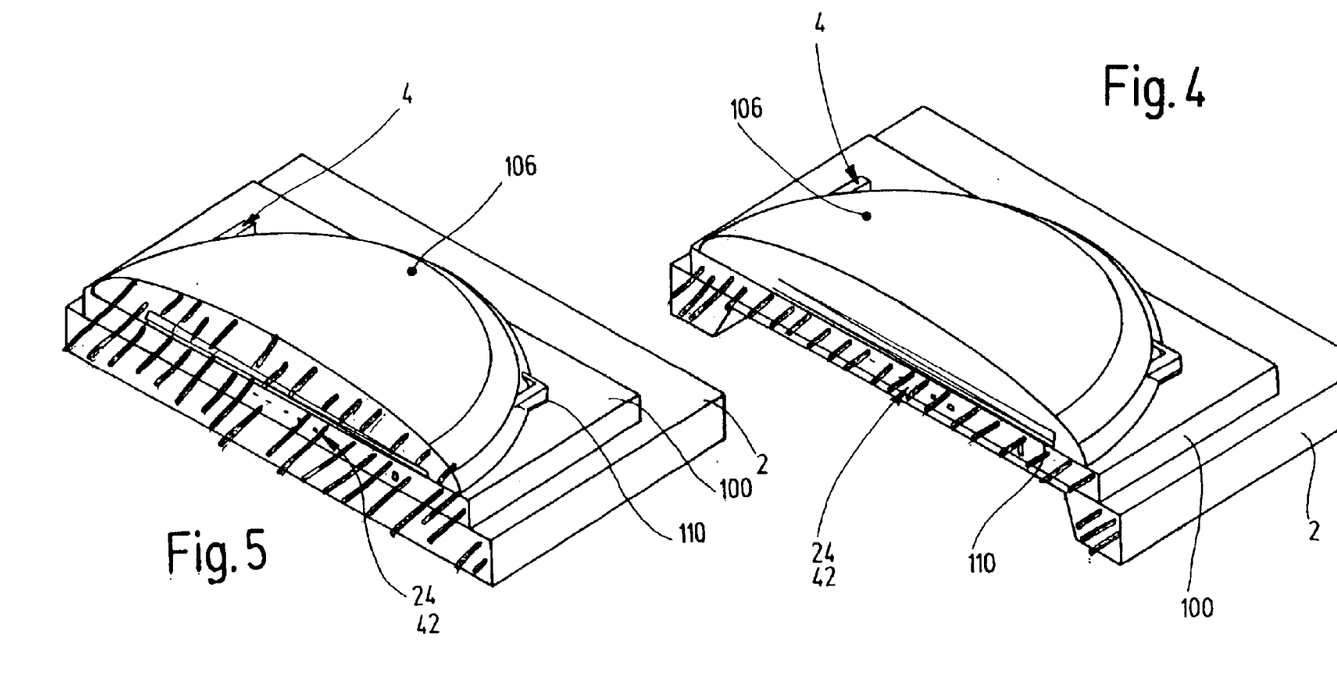
FIG. 4 shows a view of a sensor according to the present invention based on a silicon substrate, a sensitive layer being provided inside the interdigital structure.
FIG. 5 shows a view of a sensor according to the present invention based on glass, ceramic, or plastic substrates, a sensitive layer being provided inside the interdigital structure.

FIGS. 4 and 5 show a side view of a sensor according to the present invention, in which a sensitive layer 106 or a multilayer system has been deposited between interdigital electrodes 4. FIG. 4 shows an exemplary embodiment for a silicon substrate 2, while FIG. 5 depicts the arrangement for other substrate materials such as ceramic, glass, or plastic.

Figure 6:
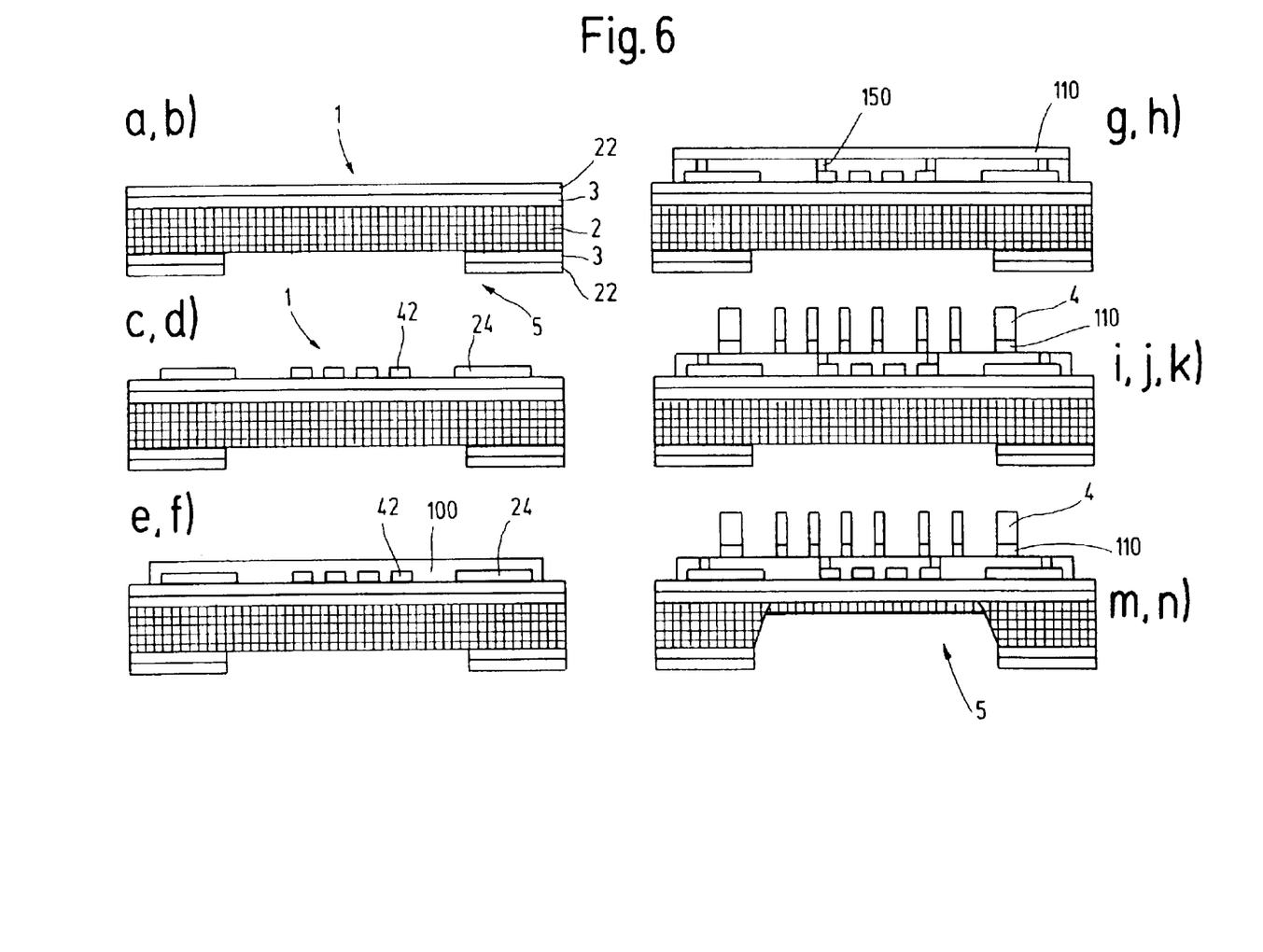
FIG. 6 illustrates the process steps for manufacturing a sensor according to the present invention.

FIG. 6 shows the manner in which a sensor according to the present invention is manufactured.

The manufacturing process, when silicon is used as substrate 2, comprises the following process steps:

a) coating silicon substrate 2 on both sides with $SiO_2$ 3 and $Si_3N_4$ 22;

b) structuring the $SiO_2$ (3) and $Si_3N_4$ (22) layer on back side 5 of the substrate (defining the region for subsequent membrane etching);

c) sputtering an adhesion layer and a metal layer (for example, platinum) onto front side 1 of the substrate;

d) structuring heating resistor 42 and temperature resistor 24;

e) depositing an insulation layer 100 onto heating resistor 42 and temperature resistor 24;

f) annealing the platinum resistor to establish and stabilize the temperature coefficient;

g) opening contact regions 150 in insulation layer 100 for heating resistor 42 and temperature resistor 24;

h) sputtering an adhesion and initiator layer 110 onto insulation layer 100;

i) structuring a thick resist layer as an electroplating form for interdigital electrodes 4;

j) electroplating metal onto the resist valleys;

k) removing the resist mask and etching initiator layer 110;

l) optionally depositing a sensitive layer inside interdigital electrodes 4;

m) membrane etching silicon substrate 2 (anisotropic etching) away from back side 5 of the substrate; and n) isolating the sensors.

When other substrate materials such as glass, ceramic, or plastic are used instead of silicon, manufacturing comprises only process steps c) through k) and n).

Process steps a) through n) will be explained in further detail below.

a) The method is based on a silicon substrate 2, polished on both sides, on which a $SiO_2$ layer 3 is first produced by thermal oxidation. LPCVD is then used to deposit a thin $Si_3N_4$ layer 22. The oxide and nitride layers serve to insulate substrate 2 and, in later steps, as an etching mask on back side 5 of the substrate. The thicknesses of the two layers are to be selected so that they form a sufficiently stable membrane when silicon substrate 2 is layer etched (process step l), and so that the tensile and compressive stresses compensate for one another within the layer system.

b) On back side 5 of the substrate, regions are photolithographically defined in which the $Si_3N_4$ is removed by a dry etching process, and the $SiO_2$ below is removed by wet chemistry. In these silicon regions which are now unmasked, the membrane will later be etched out from back side 5.

c) First an adhesion layer and then a metal layer, preferably platinum, are sputtered onto front side 1 of the substrate. Silicon can, for example, be used as the adhesion layer for platinum, but other metals (for example titanium) are also usable.

d) A resist material is applied onto the platinum layer by spin-coating or rolling, and structured using a photolithography step. The photolithographic mask used in this context contains the layout of both temperature resistor 24 and heating resistor 42. The platinum layer is etched in the resist-free regions, for example by reactive ion beam etching or by a wet chemical process. The resist mask is then removed.

e) An insulation layer 100 is applied onto the structured platinum layer, which now contains temperature resistor 24 and heating resistor 42. This layer 100 is intended to be a good electrical insulator and to have good thermal conductivity. Both CVD methods and spin-coating methods are possible as the deposition method. This insulation layer 100 serves as passivation, and is additionally intended to prevent coagulation of the platinum during the subsequent annealing step.

f) The platinum layer is artificially aged at high temperature, thus establishing the specific temperature coefficient and giving it long-term stability.

g) Using a further photolithography step, windows 150 are opened in insulation layer 100, in the region of the contact pads, by wet chemical etching. Then the photoresist is removed.

h) An adhesion and electroplating initiator layer 110 is sputtered onto front side 1 of the substrate. A layer system made up of Cr and Au, or of Ti, tungsten, and Au, can typically be used here. If requirements in terms of corrosion resistance are particularly stringent, platinum 110 is used as initiator layer 110; it can be applied in exactly the same way as onto back side 5.

i) A thick resist layer is applied by spin-coating or rolling, and is structured photolithographically or by etching. Electrode structures 4 are configured, in this process, as valleys.

j) The resist valleys are filled by electroplating. The material to be deposited depends on the particular intended application. Platinum and gold are useful as the electrode material for highly corrosive media, while silver, copper, or aluminum can also be used for less demanding requirements. Initiator layer 110, which was applied in process step h), depends on the metal being electroplated on in each case.

k) After removal of the resist layer, initiator layer 110 is removed, selectively or by differential etching, outside the electrode regions. In the process, the electrical connections between the electrodes are eliminated.

l) If so provided for the application, for example in the case of a moisture sensor or a chemically sensitive sensor, in this process step a sensitive material is deposited between interdigital electrodes 4. This can be performed, for example, using a screen-printing process, by spin-coating, or by a CVD process. Structuring of the sensitive layer using an etching step, or using photolithographic methods, may possibly be necessary.

m) Using a special etching receptacle in which front side 1 of the substrate is separated and therefore protected from the etching solution, the silicon wafer is anisotropically etched from back side 5 (KOH or TMAH etching). This step creates the membrane. The nitride/oxide layers 3, 22 structured in step b) serve as the mask.

n) After etching is complete, the sensors are isolated from the wafer by sawing.

When other substrate materials such as glass, ceramic, or plastic are used, the procedure is similar, steps a), b), l), and m) being omitted and not replaced. The only requirements placed on the substrate are good flatness and low roughness on front side 1 of the substrate.

Figure 7:
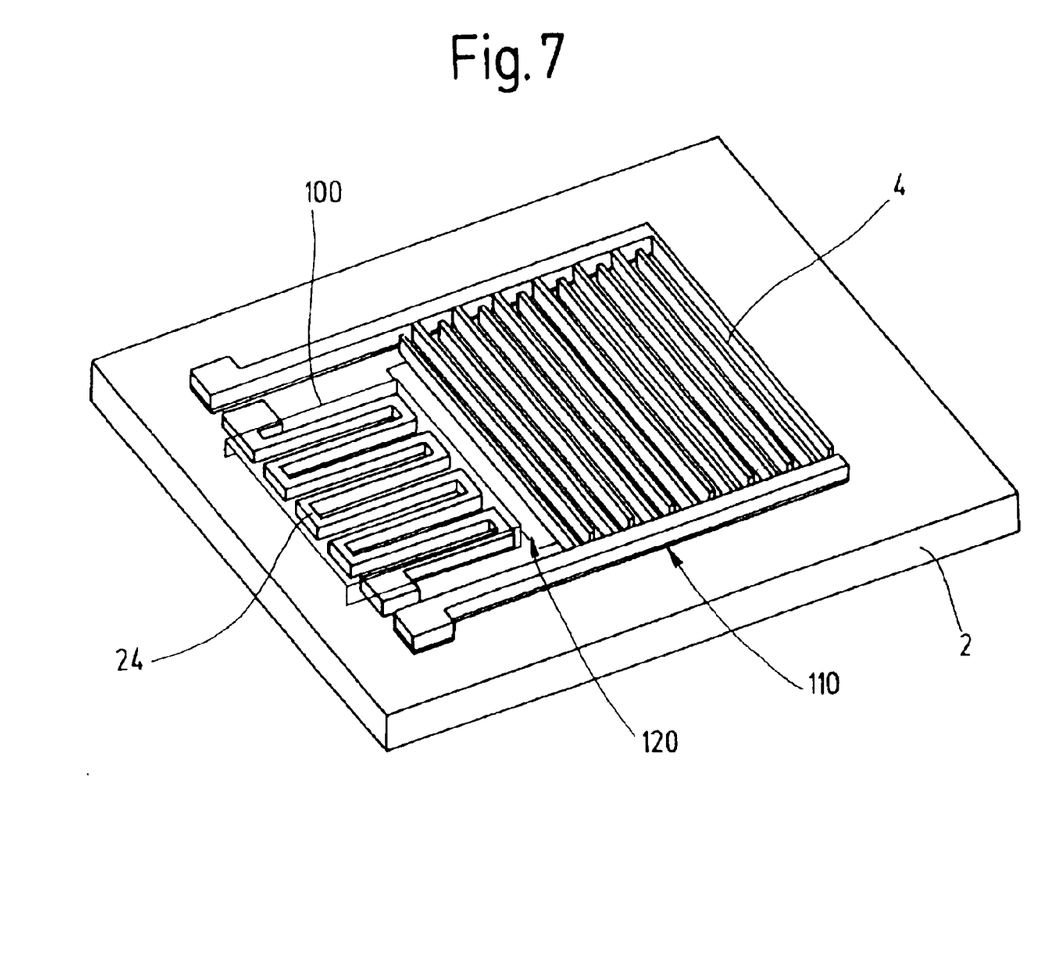
FIG. 7 shows a view of a sensor according to the present invention without a heating resistor, the temperature resistor and interdigital electrodes being located on one side of the substrate, the substrate being through-etched.

FIG. 7 shows a simplified exemplary embodiment of the sensor according to the present invention, heating resistor 42 being dispensed with. For some applications, for example the analysis of gasoline/methanol mixtures or monitoring of coolant or motor oil, heating of the fluid is not necessary. In such cases heating resistor 42 can be omitted from the overall structure. Etching of a membrane is also dispensed with, since a lower heat capacity of the sensor is then unimportant. The manufacturing sequence as described in FIG. 6 remains almost the same, since both heating resistor 42 and temperature resistor 24 are structured during one process step. Process steps b) and m) are omitted. The deletion of heating resistor 42 from the sensor structure (FIG. 7) offers the capability of also exposing interdigital electrodes 4 from the substrate side, thereby achieving better fluid contact and thus higher sensor sensitivity. Through-etching 120 of the substrate is accomplished by wet chemical means, by KOH or TMAH etching. Through-etching 120 can, of course, also be dispensed with. The procedure for manufacturing this structure is as described in FIG. 6. There are changes not only in the layout (platinum resistor 24 is not located directly beneath interdigital electrodes 4) but also in the process sequence of steps b) and m):

- b) In this process step, a window for subsequent anisotropic through-etching 120 of silicon substrate 2 in nitride layer 22 and oxide layer 3 is opened on upper side 1 of the substrate.
- m) In this manufacturing step, nitride layer 22 and oxide layer 3, which remain on upper side 1 of the substrate and are structured in step b), are used as the mask for through-etching 120 of the silicon wafer with KOH or TMAH. Since part of the mask is also removed during etching, sufficient layer thickness for the $Si_3N_4$ layer 22 and $SiO_2$ layer 3 must be guaranteed.

In addition to the arrangement of interdigital electrodes 4 and temperature resistor 24 on one substrate surface, it is also possible to arrange the two elements on different surfaces of substrate 2. This may be advantageous if temperature resistor 24, including its passivation layer 100, is not intended to come into direct contact with the fluid. In this case the present invention provides for a sensor housing in which only interdigital structure 4 comes into contact with the fluid.

Figure 8:
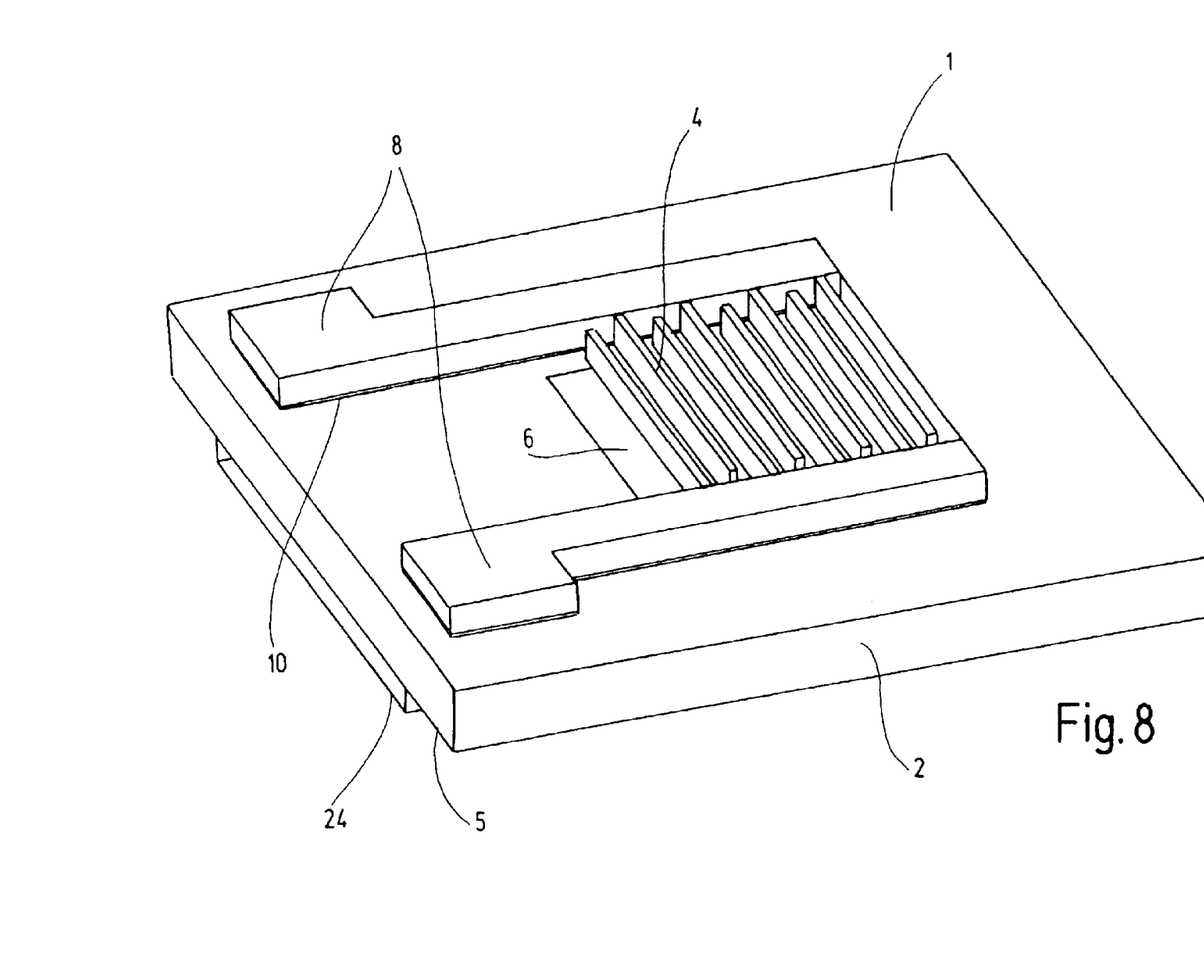
FIG. 8 shows the front side of a sensor according to the present invention, without a heating resistor, with through-etching of the substrate, the temperature resistor and interdigital electrode being located on different sides of the substrate.

FIG. 8 shows the front side of a substrate 2 made of silicon. Interdigital electrode arrangement 4, made of gold, is arranged on front side 1 between contact pads 8. Interdigital electrode arrangement 4 is arranged in a through-etched region 6 of substrate 2 which represents an opening through the entire substrate 2, so that the electrode arrangement stands exposed over the through-etched region 6. This serves to prevent contamination, and to improve coupling between the fluid and electrode arrangement 4. Also depicted is an insulation, adhesion, and contact layer 10, as well as platinum temperature resistor 24 on back side 5 of substrate 2.

Figure 9:
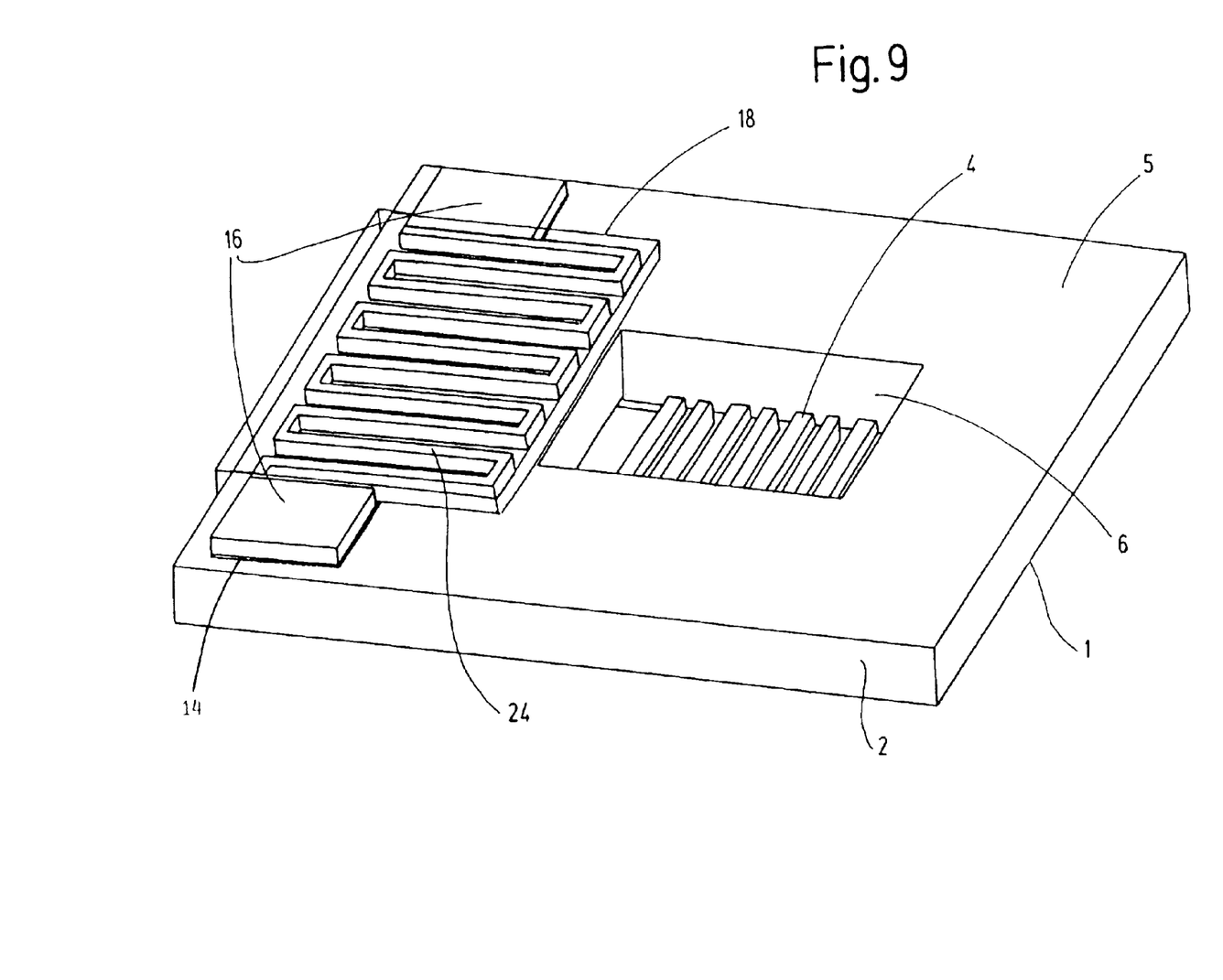
FIG. 9 shows the back side of a sensor according to the present invention, without a heating resistor, with through-etching of the substrate, the temperature resistor and interdigital electrodes being located on different sides of the substrate.

FIG. 9 depicts back side 5 of substrate 2, depicting interdigital electrode arrangement 4, visible through the through-etched region 6 and arranged on front side 1 of substrate 2. FIG. 9 further shows the arrangement of a platinum temperature resistor 24 on back side 5 of the substrate. Temperature resistor 24 is arranged in meander fashion, and serves to measure the temperature in a liquid or a gas. Temperature resistor 24 is passivated using a $SiO_2$ layer 18. Also shown are contact electrodes 16 arranged laterally with respect to temperature resistor 24, and an insulation, adhesion, and contact layer 14.

Figure 10:
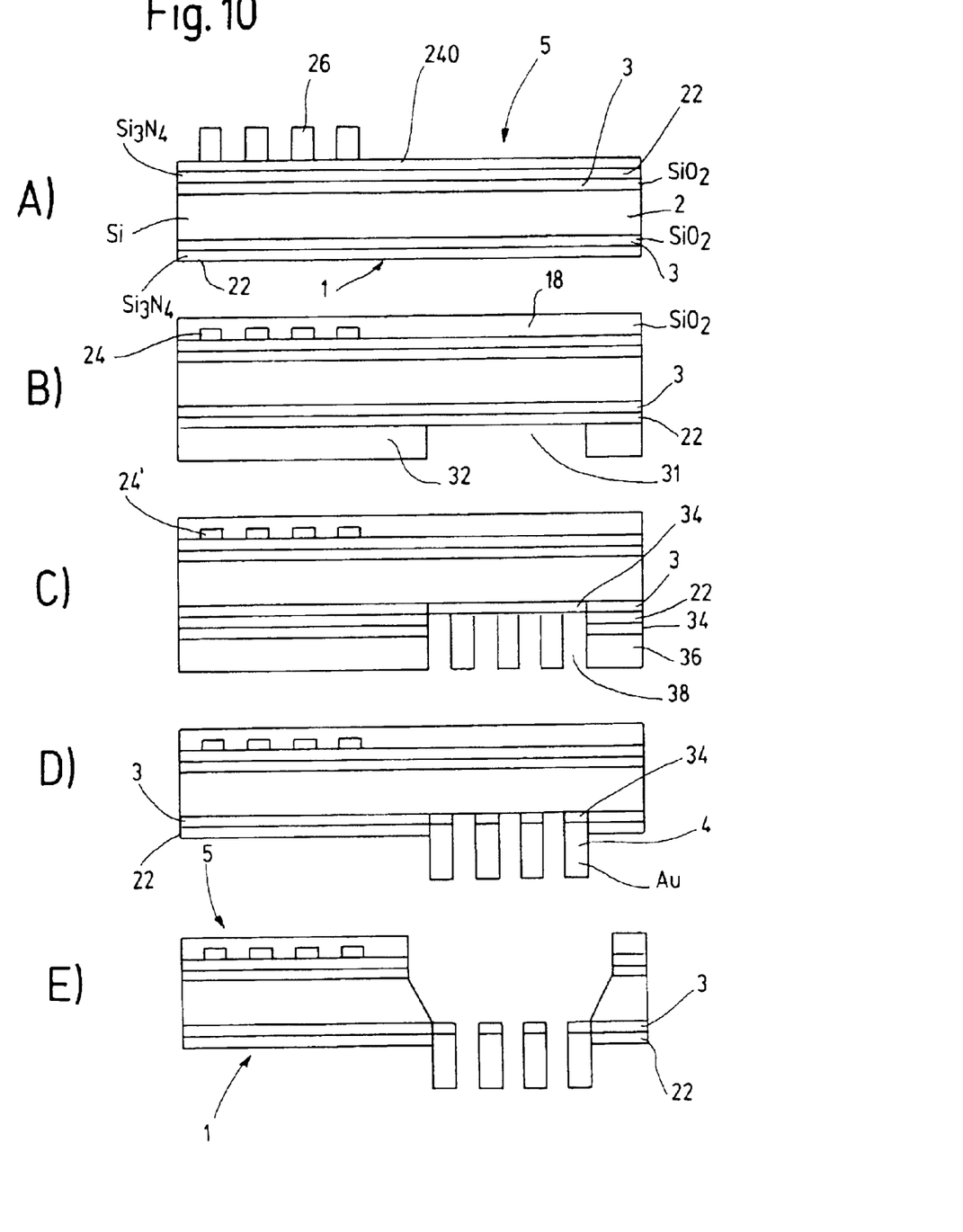
FIG. 10 illustrates the process steps for manufacturing a sensor according to the present invention without a heating resistor, structured on both sides of the substrate.

FIG. 10 shown the manner in which a sensor according to the present invention is manufactured.

It may be seen from FIG. 10A that first of all substrate 2, made of silicon and polished on both sides, is coated on both sides with $SiO_2$ and $Si_3N_4$ 22. A $SiO_2$ layer is first produced on both sides 1 and 5 of substrate 2 by thermal oxidation. Then, a thin layer 22 of $Si_3N_4$ is deposited by LPCVD, also on both surfaces 1 and 5. $SiO_2$ layers 3 and $Si_3N_4$ layers 22 serve as insulation for substrate 2 and, in later steps, as an etching mask on front side 1 of the substrate. The thicknesses of layers 3 and 22 are to be selected so that they are not completely removed upon later etching of silicon substrate 2, and the tensile and compressive stresses compensate for one another within the layer system.

An adhesion layer and then a platinum layer 240 are then sputtered onto $S_3N_4$ layer 22 arranged on back side 5 of substrate 2. Silicon can, for example, be used as the adhesion layer, although other metals such as titanium can also be used.

A resist material 26 is then applied onto platinum layer 240 by spin-coating or rolling, and structured using a photolithography or etching step. In the case of etching, an additional mask must be applied and structured. In any event, a photolithographic mask which reflects the structure of temperature resistor 24 is used for this process step. Platinum layer 240 is then etched in the resist-free regions, for example by reactive ion beam etching or by a wet chemical method. The mask of resist material 26 is then removed (FIG. 10B).

A $SiO_2$ layer 18 is then deposited, using a CVD method, onto temperature resistor 24 structured out of platinum layer 240. $SiO_2$ layer 18 serves as passivation, and is intended to prevent coagulation of the platinum during the subsequent annealing step. In the annealing step, temperature resistor 24 is artificially aged at high temperature thereby to establish the specific temperature coefficient and give it long-term stability (24', FIG. 10C).

The first process steps for manufacturing interdigital electrode arrangement 4 are also evident from FIG. 10B. First, a cutout 31 is defined photolithographically on front side 1 of the substrate using a photoresist material 32, substantially corresponding in its geometry to the through-etched region 6 of substrate 2. In addition, back side 5 of the substrate is coated with a protective varnish. In the region not protected by photoresist material 32, $SiO_2$ layer 3 and $Si_3N_4$ layer 22 are removed, which is accomplished by wet chemical etching and by dry etching. The photoresist material (not shown) is then removed from back side 5, and photoresist material 32 is removed from front side 1 of substrate 2.

An adhesion and electroplating initiator layer 34 is then sputtered onto front side 1 of substrate 2. The adhesion and electroplating initiator layer can be a layer system made up of chromium and gold, or titanium, tungsten, and gold. If requirements in terms of corrosion resistance are particularly stringent, platinum can also be used; this can be applied in the same manner as described for back side 5. Once adhesion and electroplating initiator layer 34 has been applied, a thick resist layer 36 is applied by spin-coating or rolling, and is then structured photolithographically or by etching. The structure of electrode arrangement 4 is defined in this manner as valleys 38 (FIG. 10C).

Valleys 38 are then filled up by electroplating; the metal to be deposited depends on the particular intended application (FIG. 10D). Platinum or gold may be considered as electrode material for highly corrosive media, while silver, copper, or aluminum are usable if corrosion resistance requirements are lower. The electroplating metal to be used must also be taken into account when selecting the materials to be considered for constituting adhesion and electroplating initiator layer 34.

After the removal of resist layer 36, adhesion and electroplating initiator layer 34 is removed, selectively or by differential etching, outside the electrode regions. This eliminates the electrical connections between the electrodes of electrode arrangement 4 (FIG. 10D).

Structured $Si_3N_4$ layer 22 and $SiO_2$ layer 3 which now remain on front side 1 of substrate 2 are used, in the etching step which now follows, as the mask for through-etching of substrate 2 with KOH or TMAH (FIG. 10E). A portion of layers 3 and 22 is also removed during this etching step, so that sufficient thickness for these layers must be guaranteed. Back side 5 of the sensor having platinum temperature resistor 24 must also be protected during this process step using a mask (not shown).

After completion of this etching step, in a further photolithographic process step the contact pads on back side 5 of substrate that are covered by $SiO_2$ layers are exposed, and the sensors manufactured in this fashion are isolated.

In a further exemplary embodiment, the present invention provides for the possibility of expanding the functionality of the sensor according to the present invention by depositing a sensor material in the region of electrode arrangement 4, coating electrode arrangement 4 with a sensor substance or a catalytically acting substance, or roughening electrode arrangement 4. If the interstices of electrode arrangement 4 are to be filled with a sensor substance, through-etching of substrate 2 is of course to be dispensed with.

The procedure set forth above, i.e. the combination of photolithographic and electroplating process steps, makes possible the manufacture of a sensor with high precision and at high yield. Advantageously, the sequence of process steps can be executed so that a silicon electronic analysis system can also be integrated onto substrate 2. Any desired electrode geometries, including arrays, can be implemented using the structuring method discussed. Depending on the intended application, any desired metals or metal alloys can be deposited during the electroplating process steps, so that the sensor according to the present invention can be well adapted to the medium to be characterized.

What is claimed is:

1. A method for manufacturing a sensor, the sensor including a three-dimensional interdigital electrode arrangement positioned on a substrate, the method comprising the steps of:

applying at least one of: i) a temperature sensing resistor, and ii) a heating resistor, onto the substrate by sputtering a first adhesion layer and a first metallic layer onto the substrate, applying and structuring a first resist material on the first metallic layer, and etching the first metallic layer in resist free areas; and applying a three-dimensional interdigital electrode arrangement onto the substrate, the three-dimensional interdigital electrode arrangement including a plurality of electrodes, the applying step including applying by: i) sputtering a second adhesion layer and an initiator layer onto the substrate, ii) applying and structuring a second resist material on the initiator layer to form a pattern of the three-dimensional interdigital electrode arrangement, after the structuring, iii) filling resist valleys by electroplating; and iv) after the filling, removing the second resist material, and removing the initiator layer between the electrodes of the three-dimensional electrode arrangement.

2. The method according to claim 1, wherein the substrate is a silicon substrate.

3. The method according to claim 1, wherein the at least one of the temperature sensing resistor and the heating resistor includes an integrated temperature sensing resistor.

4. The method according to claim 1, wherein the at least one of the temperature sensing resistor and the heating resistor is composed of at least one of a platinum material, a nickel material, and a TaNi material.

5. The method according to claim 1, wherein the at least one of the temperature sensing resistor and the heating resistor includes a first heating resistor.

6. The method according to claim 1, further comprising the step of:

before application of the at least one of the temperature sensing resistor and the heating resistor, and the electrode arrangement, covering a back side and a front side of the substrate with a $SiO_2$ layer and a $Si_3N_4$ layer.

7. The method according to claim 1, wherein the first metallic layer includes one of a platinum layer, a nickel layer, and a TaNi layer; and wherein the method further comprises:

passivating the at least one of the temperature sensing resistor and the heating resistor; and annealing the at least one of the temperature sensing resistor and the heating resistor.

8. The method according to claim 7, wherein the at least one of the temperature sensing resistor and the heating resistor is applied onto a back side of the substrate.

9. The method according to claim 1, wherein the at least one of the temperature sensing resistor and heating resistor is applied onto a first surface of the substrate and the three-dimensional interdigital electrode arrangement is applied onto a second surface of the substrate, the second surface being different than the first surface.

10. The method according to claim 9, wherein the second surface is opposite to the first surface.

11. The method according to claim 1, wherein the at least one of the temperature sensing resistor and the heating resistor is electrically separate from the three-dimensional interdigital electrode arrangement.

12. The method according to claim 1, wherein the three-dimensional interdigital electrode arrangement is applied to the substrate over the at least one of a temperature sensing resistor and a heating resistor.

13. A method for making a sensor for measuring conductivity or capacitance of gases or liquids, comprising:

sputtering an adhesion layer and an initiator layer onto a substrate;

applying and structuring a resist layer onto the initiator layer to form a pattern of the metallic three-dimensional interdigital electrode arrangement, the metallic three-dimensional interdigital electrode arrangement including a plurality of electrodes;

electroplating grooves in the resist layer to form a metallic three-dimensional interdigital electrode arrangement; and after the electroplating, removing the resist layer, and removing the initiator layer between the electrodes of the metallic three-dimensional interdigital electrode arrangement.

14. The method according to claim 13, further comprising:

forming an integrated heating resistor on the substrate.

15. The method according to claim 13, further comprising:

forming an integrated temperature sensing resistor on the substrate.

16. The method according to claim 15, wherein the step of forming the temperature sensing resistor includes forming the temperature sensing resistor from one of platinum, nickel, and TaNi.

17. The method according to claim 15, wherein the step of forming the temperature sensing resistor includes forming the integrated temperature sensing resistor on a backside of the substrate.

18. The method according to claim 13, further comprising:

providing the substrate, the substrate including at least one of a glass material, a plastic material, a ceramic material, and a silicon material.

19. The method according to claim 13, wherein the step of electroplating the grooves includes electroplating the grooves in a region of the substrate which is removed, at least in part, by etching in a later process step.

20. The method according to claim 13, wherein the steps of sputtering, applying and structuring, electroplating and removing are performed on a front side of the substrate.

21. The method according to claim 13, further comprising:
   positioning one of a sensitive layer and a multilayer system between the electrodes, one a capacitance and conductivity of the one of the sensitive layer and the multilayer system changing in accordance with a penetration of one of a gas and a fluid.

22. The method according to claim 13, wherein the step of electroplating the grooves includes electroplating the grooves in the resist layer to form the metallic three-dimensional interdigital electrode arrangement, a height of the electrodes being greater than a width of the electrodes.

23. A method for manufacturing a sensor, the sensor including a three-dimensional interdigital electrode arrangement positioned on a substrate, the method comprising the steps of:
   applying at least one of a temperature sensing resistor and a heating resistor onto the substrate by sputtering a first adhesion layer and a first metallic layer onto the substrate, applying and structuring a first resist material on the first metallic layer, and etching the first metallic layer in resist free areas; and
   applying a three-dimensional interdigital electrode arrangement onto the substrate, the three-dimensional interdigital electrode arrangement including a plurality of electrodes, each of the electrodes having vertical surfaces and a horizontal surface, the vertical surfaces extending vertically from a surface of the substrate, the horizontal surface being horizontal relative to the surface of the substrate, the three-dimensional interdigital electrode being applied onto the substrate by: i) sputtering a second adhesion layer and an initiator layer onto the substrate, ii) applying and structuring a second resist material on the initiator layer to form a pattern of the three-dimensional interdigital electrode arrangement having fingers, after the structuring, iii) filling resist valleys by electroplating; and iv) after the filling, removing the second resist material, and removing the initiator layer between the fingers of the three-dimensional electrode arrangement;
   wherein the three-dimensional interdigital electrode is applied so that for each of the electrodes, a surface area of the vertical surfaces is larger than a surface area of the horizontal surface.

24. A method for making a sensor for measuring conductivity or capacitance of gases or liquids, comprising:
   sputtering an adhesion layer and an initiator layer onto a substrate;
   applying and structuring a resist layer onto the initiator layer to form a pattern of the metallic three-dimensional interdigital electrode arrangement having a plurality of electrodes, each of the electrodes having vertical surfaces and a horizontal surface, the vertical surfaces extending vertically from a surface of the substrate, and the horizontal surface being horizontal relative to the surface of the substrate;
   electroplating grooves in the resist layer to form a metallic three-dimensional interdigital electrode arrangement so that for each of the electrodes, a surface area of the vertical surfaces is larger than a surface area of the horizontal surface; and
   after the electroplating, removing the resist layer, and removing the initiator layer between the fingers of the metallic three-dimensional interdigital electrode arrangement.

25. A method for making a sensor for measuring conductivity or capacitance of gases or liquids, comprising:
   sputtering an adhesion layer and an initiator layer onto the substrate;
   applying and structuring a resist layer onto the initiator layer to form a pattern of a metallic three-dimensional interdigital electrode arrangement having a plurality of electrodes, each of the electrodes having vertical surfaces and a horizontal surface, the vertical surfaces extending vertically from a surface of the substrate, and the horizontal surface being horizontal to and spaced from the surface of the substrate; electroplating grooves in the resist layer to form a metallic three-dimensional interdigital electrode arrangement so that for each of the electrodes, a height of the vertical surface is larger than a width of the horizontal surface; and
   after the electroplating, removing the resist layer, and removing the initiator layer between the fingers of the metallic three-dimensional interdigital electrode arrangement.

* * * * *

UNITED STATES PATENT AND TRADEMARK OFFICE
CERTIFICATE OF CORRECTION

PATENT NO.   : 6,787,047 B1
DATED        : September 7, 2004
INVENTOR(S)  : Dietmar Hahn et al.

It is certified that error appears in the above-identified patent and that said Letters Patent is hereby corrected as shown below:

<u>Title page, Item [54] and Column 1, line 1,</u>
Title, change from "METHODS FOR MANUFACTURING A MICROSTRUCTURED SENSOR" to -- METHOD FOR MANUFACTURING A MICROSTRUCTURED SENSOR --

<u>Column 2,</u>
Line 40, change "beat input" to -- heat input --

Signed and Sealed this

Twelfth Day of July, 2005

JON W. DUDAS
*Director of the United States Patent and Trademark Office*